US00PP35835P2

(12) United States Plant Patent
Hara

(10) Patent No.: US PP35,835 P2
(45) Date of Patent: May 28, 2024

(54) ***HYDRANGEA* PLANT NAMED 'HYSO22'**

(50) Latin Name: *Hydrangea arborescens*
Varietal Denomination: Hyso22

(71) Applicant: Toshihiko Hara, Kuruma (JP)

(72) Inventor: Toshihiko Hara, Kuruma (JP)

( * ) Notice: Subject to any disclaimer, the term of this patent is extended or adjusted under 35 U.S.C. 154(b) by 0 days.

(21) Appl. No.: 18/370,475

(22) Filed: Sep. 20, 2023

(30) Foreign Application Priority Data

Sep. 7, 2023 (QZ) ..... PBR 20231861

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Penny J. Aguirre

(57) ABSTRACT

A new cultivar of *Hydrangea arborescens* plant named 'Hyso22' that is characterized by its sturdy stems, its medium sized, its compact plant habit, and its inflorescence that start dark pink in color, change to a blend of light and dark pink, and then change to pink with green undertones.

3 Drawing Sheets

Botanical classification: *Hydrangea arborescens*.
Varietal denomination: 'Hyso22'.

CROSS REFERENCE TO A RELATED APPLICATION

This application claims priority to European Community Plant Variety Office (CPVO) Plant Breeder's Rights Application No. 2023/1861, filed on Sep. 7, 2023, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Hydrangea arborescens* and will be referred to hereafter by its cultivar name, 'Hyso22'. 'Hyso22' represents a new smooth *Hydrangea*, a perennial shrub grown for landscape use.

'Hyso22' was discovered as a chance seedling in a production field of *Hydrangea arborescens* in Kuruma, Kukuoka, Japan in summer of 2016. The parents are unknown.

Asexual propagation of the new cultivar was first accomplished by stem cuttings by the Inventor in summer of 2016 in Kuruma, Kukuoka, Japan. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hyso22' as a unique cultivar of *Hydrangea arborescens*.

1. 'Hyso22' exhibits sturdy stems.
2. 'Hyso22' exhibits a medium sized, compact plant habit.

3. 'Hyso22' exhibits inflorescence colors that start dark pink in color, change to a blend of light and dark pink, and then change to pink with green undertones.

'Hyso22' can be compared to *Hydrangea arborescens* cultivars 'GRHYAR1407' (U.S. Plant Pat. No. 31,016) and 'NCHA3' (U.S. Plant Pat. No. 28,317). 'GRHYAR1407' is similar to 'Hyso22' in having strong stems and a similar plant habit. 'GRHYAR1407' differs from 'Hyso22' in having inflorescences that are larger in size and sterile sepals that are lighter pink in color, larger in size, and less slender. 'NCHA3' differs from 'Hyso22' in having inflorescences with larger sterile flowers with sterile sepals that are broader and mature in color with less green undertones, and in having a more compact plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantago, Arboretum Wojslawice, Plantipp, Garden 4 you, Zahradnictvispomysl, Nezabravka Flowers, Promesse de Fleurs, Garten Schluter, Zelenabuhta, Parko Medelynas, Balsad, Daglezja na Zielonej, Mein Garten Shop, Rasadnik Topalovic, Sadpoltava, Pflanzmich, Garten Sauer, Tuin Flora, Jardin Pour Vous, Paridise Place, Katanor pactehnn, Die Nr-01, Hortenzija, Forum sibmama, Forum House, Biud Market, Moga, Juhani Puukool, Zbozi, Abyhom, Gartenstauden, Posadka, Semsad, Reg Markets, Web Shopy, Ozon, Yesipova, Sad-i-ogorod, Sibdachnik, Crocus, and Pulkovsad.

BRIEF DESCRIPTION OF THE DRAWINGS

The accompanying color photographs illustrate the overall appearance and distinct characteristics of the new

*Hydrangea*. The photographs in FIG. 1, FIG. 2, and FIG. 3 were taken of plants three years in age as grown outdoors in 3-liter containers in Ederveen, The Netherlands.

Figure 1:
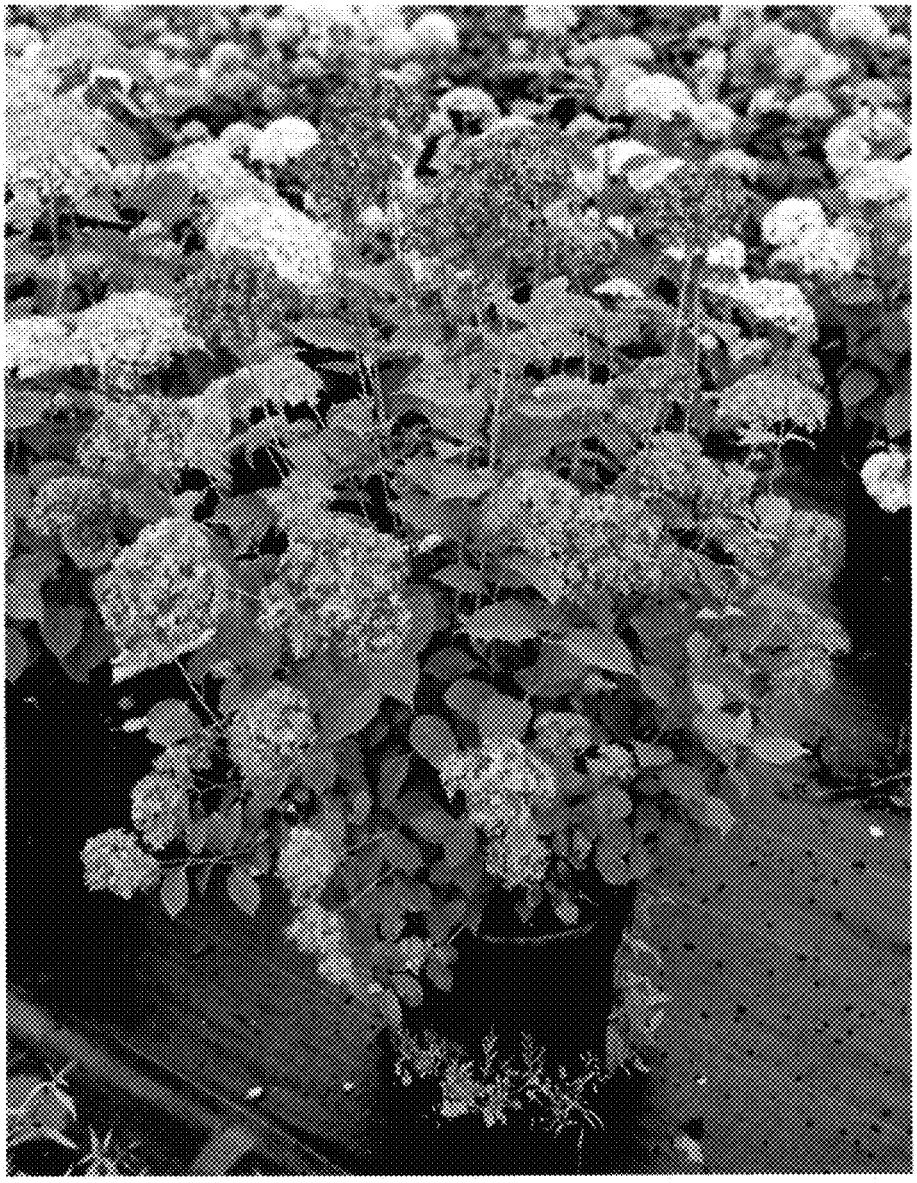

The photograph in FIG. 1 provides a side view of a plant of 'Hyso22' in bloom.

Figure 2:
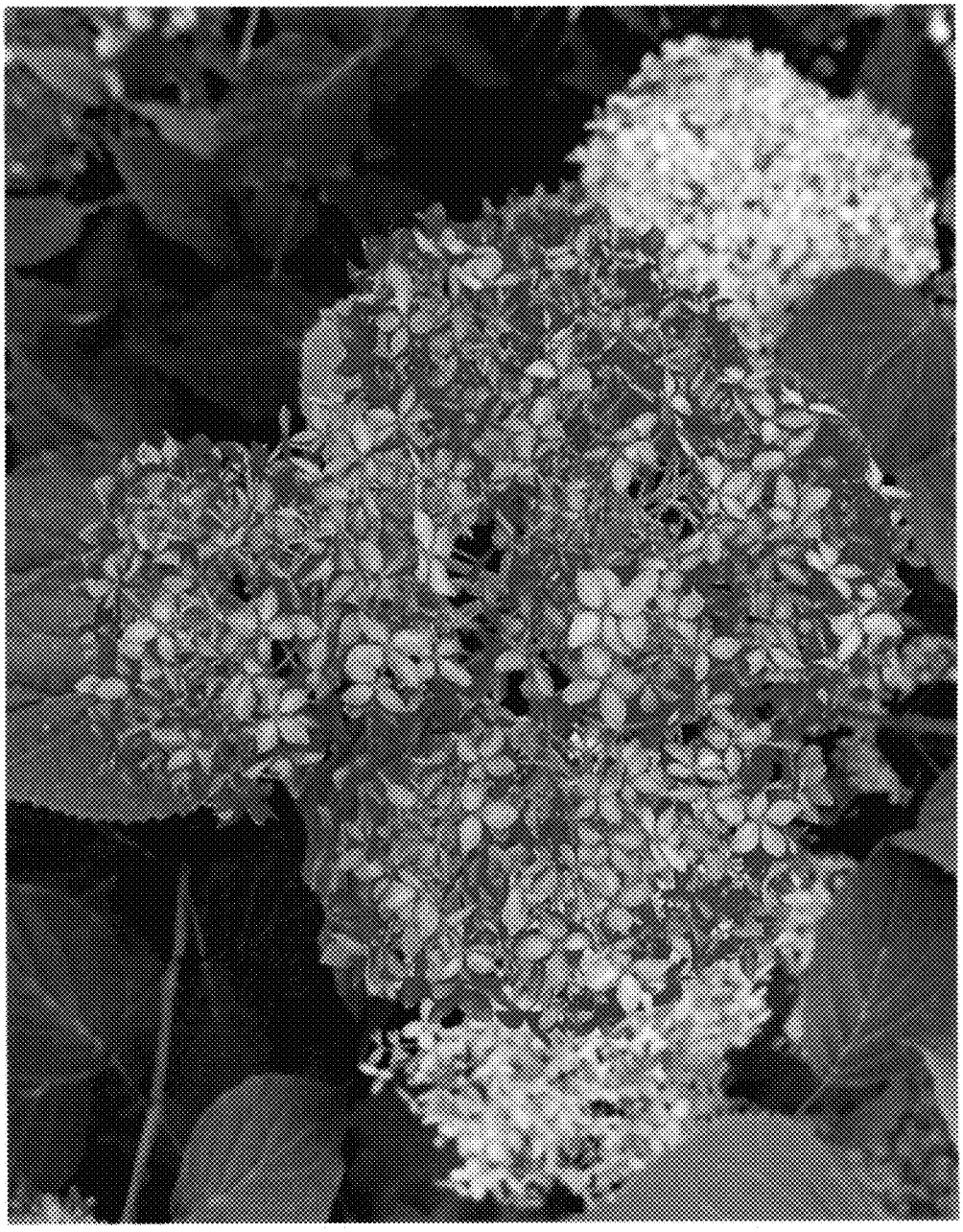

The photograph in FIG. 2 provides a view of the inflorescences of 'Hyso22' (opening and maturing).

Figure 3:
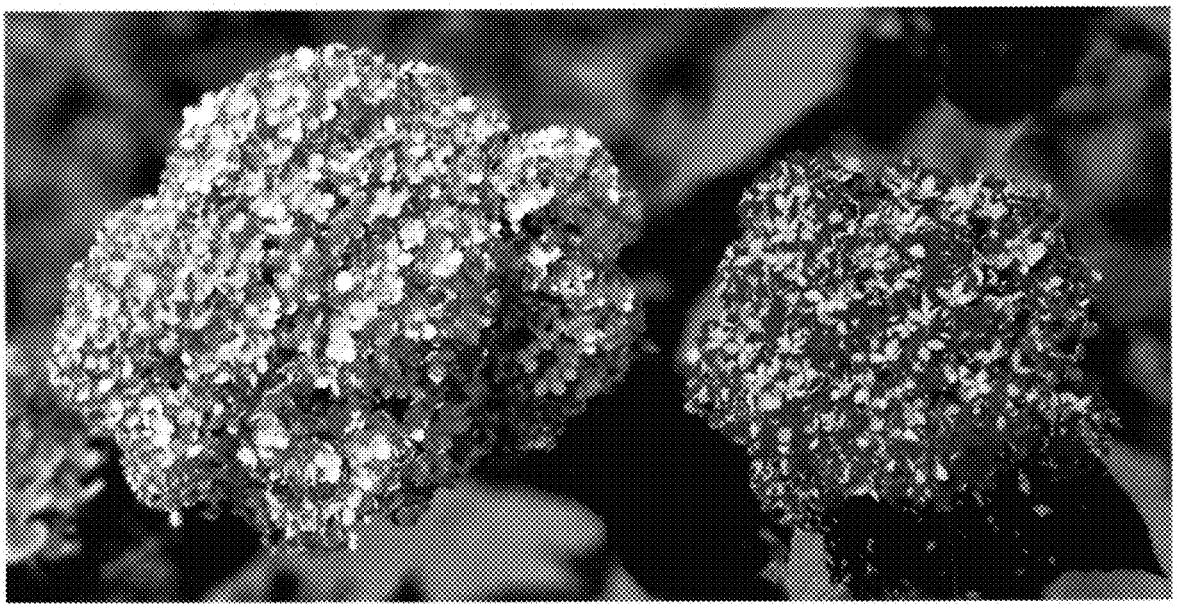

The photograph in FIG. 3 provides a comparison of an inflorescence of 'GRHYAR1407' (left) and 'Hyso22' (right).

Figure 4:
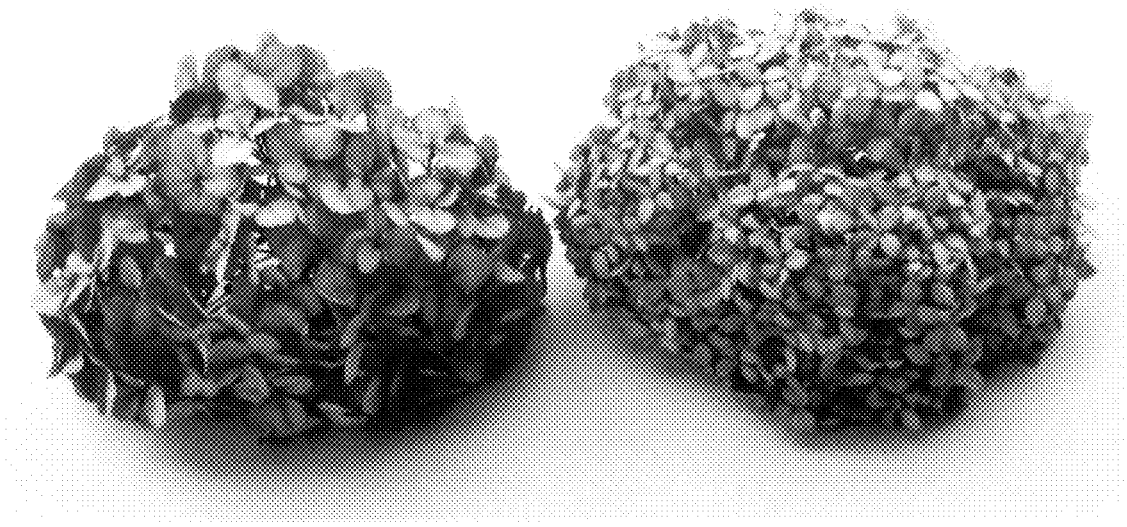

The photograph in FIG. 4 was taken of plants 2-years in age as grown outdoors in a trail bed in Boskoop, The Netherlands and provides a comparison of an inflorescence of 'NCHA3' (left) and 'Hyso22' (right).

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants three years in age as field grown in Geldermalsen, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—July to September in The Netherlands.

*Plant type.*—Perennial shrub with mophead-like inflorescences.

*Plant habit.*—Sturdy stems, compact, obovate in shape.

*Height and spread.*—Average of 1.1 m in height, 1.2 m in width as a mature plant in the landscape.

*Cold hardiness.*—At least to U.S.D.A. Zones 5b.

*Diseases and pests.*—No susceptibility and resistance to pests and diseases has been observed.

*Root description.*—Fibrous, N155D in color.

*Root development.*—6 to 8 weeks for root initiation with a plant finished in a P9 container in about 12 months from a rooted cutting.

*Growth rate.*—Vigorous.

Stem description:

*Stem shape.*—Round.

*Stem color.*—New growth; 144C, flushed with 175B, mature wood and bark; N199C to 199D.

*Stem size.*—52 to 72 cm in length and 7 mm in diameter.

*Stem surface.*—Glabrous, mature wood; smooth, no fasciation.

*Stem aspect.*—Vertical to outward.

*Internode length.*—10 to 12 cm.

*Branching.*—Average of 20 to 25 branches from base.

*Stem strength.*—Strong.

Foliage description:

*Leaf shape.*—Broadly ovate.

*Leaf division.*—Simple.

*Leaf size.*—Up to 10 cm in length and 7 cm in width.

*Leaf base.*—Rounded.

*Leaf apex.*—Acuminate.

*Leaf venation.*—Pinnate, upper surface 144A, lower surface 144B.

*Leaf margins.*—Serrate.

*Leaf attachment.*—Petiolate.

*Leaf arrangement.*—Opposite.

*Leaf surface.*—Both surfaces slightly pubescent, slightly glossy.

*Leaf color.*—Immature leaves upper surface; 144A, immature leaves lower surface; 146B, mature leaves upper surface; NN137A, mature leaves lower surface; NN137C.

*Petioles.*—3 cm in length and 2 mm in diameter, both surfaces slightly pubescent, upper surface color 144C, flushed with 175B, lower surface color 144C.

Inflorescence description:

*Inflorescence type.*—Terminal mop-head; cymose corymb, comprised of showy flowers and fertile flowers.

*Lastingness of inflorescence.*—Up to 8 weeks in color.

*Inflorescence number.*—One per stem.

*Inflorescence size.*—Average of 10 cm in height and 16 cm in diameter.

*Flower fragrance.*—No fragrance.

*Flower buds.*—Sterile flowers; 2 mm in length, 1 mm in diameter, ovate in shape, 59C to 59D in color, fertile flowers; 2 mm in length and diameter, round in shape, 63C in color.

*Flowers.*—Sterile; 200 to 300 per inflorescence, fertile; average of 100 per inflorescence.

*Peduncles.*—Strong, 1 to 4 cm in length and 1 to 2.5 mm in width, 145C to 145D in color, surface dense short hairy.

*Pedicels.*—Sterile flowers; 1 cm to 1 mm in diameter, strong, color; 145B, flushed with 61A to 61B, surface is smooth, fertile flowers; 3 mm in length, 1 mm in width, typically held upright, moderately strong, 145C to 145D in color, surface is slightly pubescent.

*Petals.*—Sterile flowers; 4, comprise center spot, cymbiform in shape, entire margin, acute apex with obtuse tip, obtuse base, average of 1 mm in length and width, upper and lower surface glabrous, color; matches sepal color, fertile flowers; 5, rotate in arrangement, ovate in shape, an average of 1 mm in length and width, acute apex, truncate base, entire margins, upper and lower surface glabrous, color; upper surface 63D, lower surface 63C to 63D.

*Sepals.*—Sterile flowers; typically 4 (occasionally 3 or 4), rotate in arrangement, elliptical in shape, entire margin, acute apex, obtuse base, 8 mm in length, 5 mm in width, both surfaces glabrous, color; upper and lower surface when opening and fully open 61A to 61B, maturing upper surface 63C to 63D, margins and veins 63A to 63B, maturing lower surface 63A to 63C, older sepals turn to a blend of 157A to 63B on both surfaces, fertile flowers; 5, rotate in arrangement, elliptic in shape, acute apex, cuneate base, entire margin, an average of 2 mm in length and 1.5 cm in width, both surfaces glabrous and matte, color; upper and lower surface when opening and fully open 158D, quickly fleeting.

Reproductive organs:

*Presence.*—Fertile flowers.

*Stamens.*—9 to 10, filament is 3 mm in length and NN155D in color, anther is round in shape, 0.8 mm in length and NN155D in color, no pollen was observed.

*Pistils.*—2, an average of 1 mm in length, stigma is round in shape, stigma, style, and ovary are NN155D in color.

*Fruit and seed.*—No fruit or seed production has been observed to date.

It is claimed:

1. A new and distinct cultivar of *Hydrangea* plant named 'Hyso22' substantially as herein illustrated and described.

* * * * *